US008124936B1

(12) United States Patent
Lagna

(10) Patent No.: US 8,124,936 B1
(45) Date of Patent: Feb. 28, 2012

(54) STAND-OFF CHEMICAL DETECTOR

(75) Inventor: William M. Lagna, Baltimore, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 448 days.

(21) Appl. No.: 11/955,674

(22) Filed: Dec. 13, 2007

(51) Int. Cl.
*H01L 27/14* (2006.01)

(52) U.S. Cl. .................................. 250/339.01; 250/372

(58) Field of Classification Search ............. 250/339.1, 250/339, 372
See application file for complete search history.

(56) References Cited

U.S. PATENT DOCUMENTS

| | | | | |
|---|---|---|---|---|
| 5,512,748 | A * | 4/1996 | Hanson | 250/332 |
| 5,925,883 | A * | 7/1999 | Woolaway, II | 250/370.08 |
| 6,198,532 | B1 * | 3/2001 | Cabib et al. | 356/456 |
| 6,573,503 | B1 * | 6/2003 | Bawolek et al. | 250/332 |
| 6,770,882 | B2 * | 8/2004 | Carr et al. | 250/338.1 |
| 7,193,210 | B2 * | 3/2007 | Garber et al. | 250/330 |
| 7,247,892 | B2 * | 7/2007 | Taylor | 257/197 |
| 7,432,539 | B2 * | 10/2008 | Taylor | 257/197 |
| 7,504,993 | B2 * | 3/2009 | Young et al. | 342/179 |
| 7,592,593 | B2 * | 9/2009 | Kauffman et al. | 250/332 |
| 2003/0020099 | A1 * | 1/2003 | Taylor | 257/215 |
| 2004/0079971 | A1 * | 4/2004 | Taylor | 257/215 |
| 2005/0082480 | A1 * | 4/2005 | Wagner et al. | 250/338.1 |
| 2006/0022139 | A1 * | 2/2006 | Garber et al. | 250/330 |
| 2007/0023661 | A1 * | 2/2007 | Wagner et al. | 250/338.1 |
| 2007/0081156 | A1 * | 4/2007 | Treado et al. | 356/301 |
| 2008/0246950 | A1 * | 10/2008 | Ono | 356/51 |
| 2009/0009654 | A1 * | 1/2009 | Imai et al. | 348/360 |
| 2009/0040099 | A1 * | 2/2009 | Young et al. | 342/179 |
| 2009/0141974 | A1 * | 6/2009 | Ono | 382/165 |
| 2009/0173883 | A1 * | 7/2009 | Kauffman et al. | 250/338.4 |

\* cited by examiner

*Primary Examiner* — David Porta
*Assistant Examiner* — Djura Malevic
(74) *Attorney, Agent, or Firm* — Ulysses John Biffoni

(57) ABSTRACT

A stand-off chemical detector has an array of charge-coupled-device electromagnetic radiation sensing elements. One or more first charge-coupled-device electromagnetic radiation sensing elements of the array are selectively responsive to non-visible electromagnetic radiation having at least a first wavelength, and one or more second charge-coupled-device electromagnetic radiation sensing elements of the array are selectively responsive to non-visible electromagnetic radiation having at least a second wavelength that is different that the at least first wavelength.

25 Claims, 3 Drawing Sheets

| $C_1$ | $C_2$ | $C_1$ | $C_2$ | $C_1$ | $C_2$ |
|---|---|---|---|---|---|
| $C_3$ | $C_1$ | $C_3$ | $C_1$ | $C_3$ | $C_1$ |
| $C_1$ | $C_2$ | $C_1$ | $C_2$ | $C_1$ | $C_2$ |
| $C_3$ | $C_1$ | $C_3$ | $C_1$ | $C_3$ | $C_1$ |
| $C_1$ | $C_2$ | $C_1$ | $C_2$ | $C_1$ | $C_2$ |
| $C_3$ | $C_1$ | $C_3$ | $C_1$ | $C_3$ | $C_1$ |

STAND-OFF CHEMICAL DETECTOR

GOVERNMENT INTEREST

The invention described herein may be manufactured, licensed, and used by or for the U.S. Government.

TECHNICAL FIELD

The present invention relates to chemical detectors, and, in particular, to stand-off chemical detectors.

BACKGROUND

Chemical compounds, such as explosives, chemical warfare agents, and other hazardous materials pose hazards to conventional military forces and to civilian populations, thus making the detection of these compounds imperative. Explosives used in the manufacture of explosive devices, such as Improvised Explosive Devices (IEDs), chemical agents, and many hazardous chemicals, have unique chemical signatures in the electromagnetic-radiation-wavelength range between about 1 and about 4 microns. Therefore, electromagnetic-radiation-based chemical detectors are often used to detect such chemical signatures.

Some conventional electromagnetic-radiation-based chemical detectors used for detecting chemical compounds use expensive and non-uniform mercury cadmium telluride (HgCdTe) detectors, various types of quantum well infrared (QWIP/QWID) photodetectors with special cooling needs, or Indium Gallium Arsenide (InAs—GaAs) or Indium phosphide (InP) based detectors to detect chemical compounds in wavelength region between about 1 and about 4 microns. In addition to high manufacturing costs, the imaging qualities of these detectors are relatively poor, and these detectors require specialized software to accomplish the signal processing.

Another electromagnetic-radiation-based chemical detection technique, up-converts mid-infrared photons to near-infrared photons for detection by standard Charge Coupled Devices (CCDs), which can image into the near-infrared region. Using this technique, electron hole pairs are optically generated. On excitation using an electric field, the holes escape in the near-infrared region, while the electrons escape in the mid-infrared region. Although this approach has unique advantages, it is complex.

Differentiating the unique chemical signatures of target chemical compounds, such as explosives, chemical agents, hazardous chemicals, etc., also presents a problem. For example, many conventional electromagnetic-radiation-based chemical detectors use a grating or a Michelson interferometer to break the electromagnetic radiation over the wavelength region between about 1 and about 4 microns into useful spectra. This approach is impractical for high-speed, high-resolution imaging, however.

SUMMARY

One embodiment provides a stand-off chemical detector having an array of charge-coupled-device electromagnetic radiation sensing elements. One or more first charge-coupled-device electromagnetic radiation sensing elements of the array are selectively responsive to non-visible electromagnetic radiation having at least a first wavelength, and one or more second charge-coupled-device electromagnetic radiation sensing elements of the array are selectively responsive to non-visible electromagnetic radiation having at least a second wavelength that is different from the at least first wavelength. For other embodiments, the stand-off detector may include additional charge-coupled-device electromagnetic radiation sensing elements that are selectively responsive to one or more additional wavelengths that are different than the at least first and the at least second wavelengths.

BRIEF DESCRIPTION OF THE DRAWINGS

FIG. 3 illustrates an example of an image pattern, according to another embodiment of the disclosure.

DETAILED DESCRIPTION

Figure 1:
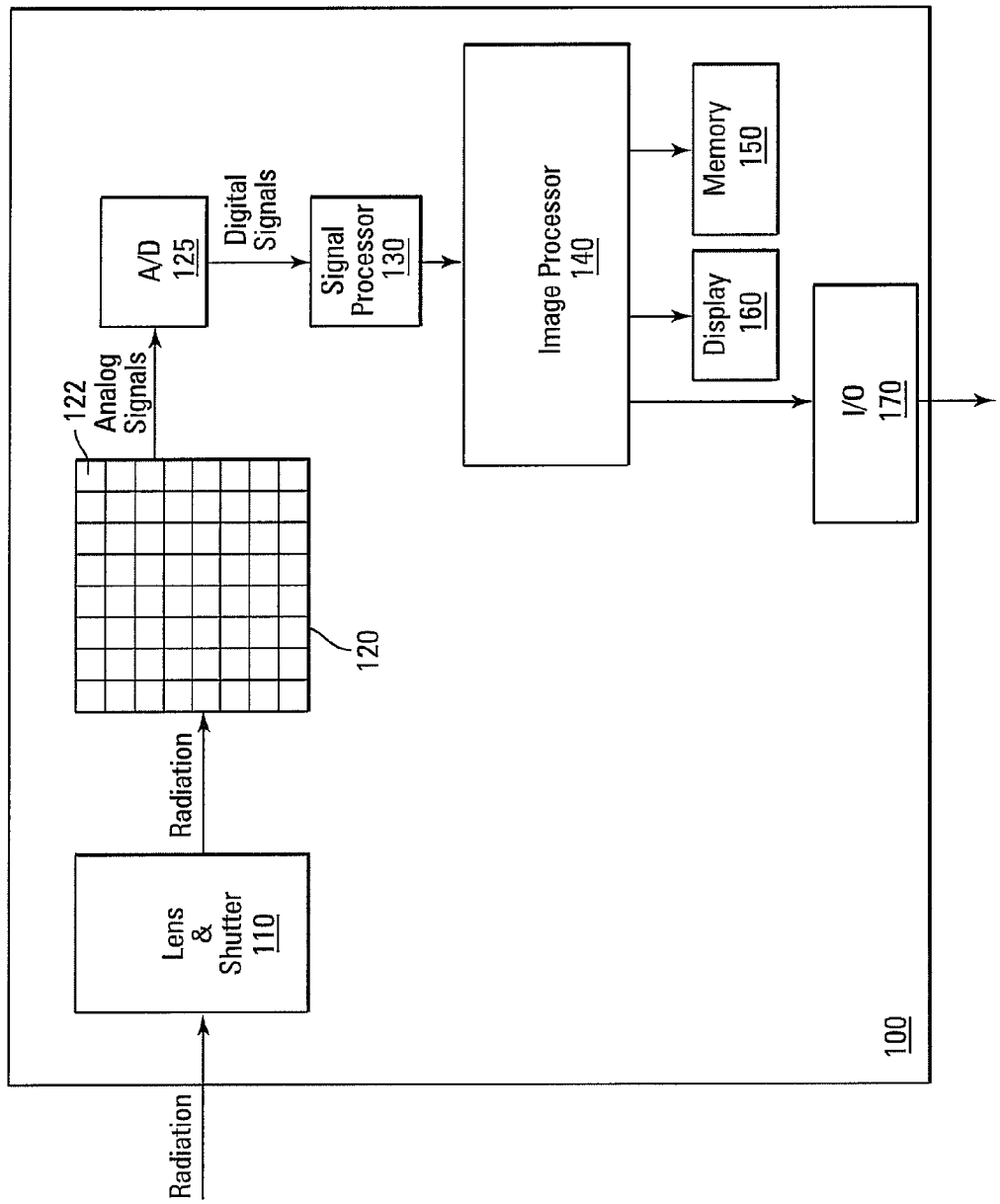
FIG. 1 is a block diagram illustration of an embodiment of a stand-off chemical detector, according to an embodiment of the disclosure.

In the following detailed description, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice these embodiments. Other embodiments may be utilized and structural, logical, and electrical changes may be made without departing from the scope of the present disclosure.

FIG. 1 is a block diagram illustrating a stand-off chemical detector 100, according to an embodiment. In operation, electromagnetic radiation from objects in an image field (or field-of-view) of detector 100 is received at a lens-and-shutter system 110 of detector 100. Lens-and-shutter system 110 focuses the radiation onto an array 120 of radiation sensing elements, e.g., Charged Coupled Device (CCD) radiation sensing elements 122, where the sensing elements 122 respectively correspond (correspond one-to-one) to pixels of the image field of chemical detector 100.

The radiation is filtered before arriving at each radiation sensing element. For one embodiment, each sensing element may be coated with a filter to yield a spectral output or signal with a peak at a certain (e.g., predetermined) wavelength. For example, red, blue, and green filters may be used to respectively yield spectral signals with peaks for red, blue, and green light portions of the visible region of the electromagnetic spectrum.

For one embodiment, additional filters may be used to extend the detection range to the non-visible infrared region for detecting chemical compounds, such as explosives, e.g., n-nitroso compounds, having chemical signatures at wavelengths in the non-visible infrared region. For example, infrared filters may be used to yield spectral signals with peaks at wavelengths in the near-infrared region (e.g., about 0.75 to about 5 microns) and mid-infrared region (e.g., about 5 to about 15 microns). For one embodiment, infrared filters may be used to yield spectral signals with peaks at least wavelengths of about 1.2, 1.9, 2.5, and 3.3 microns. These infrared filters can pass substantially only or only infrared radiation and can block substantially all other radiation. Such filters may include aluminum-gallium-arsenide blocking layers formed on respective ones of the radiation sensing elements, for example.

For another embodiment, ultraviolet filters may be used to extend the detection range to the non-visible near ultraviolet region (e.g., about 0.35 to about 0.2 microns) to yield spectral signals with peaks at wavelengths in the ultraviolet region for detecting chemical compounds having chemical signatures at wavelengths in the ultraviolet region. These ultraviolet filters can pass substantially only or only ultraviolet radiation and can block substantially all other radiation. An example of a suitable ultraviolet filter may be a germanium coating formed on respective ones of the radiation sensing elements.

For one embodiment, the infrared and ultraviolet filters configure array 120 for detecting radiation with wavelengths of about 0.35 to about 4 microns. For another embodiment, the infrared and/or ultraviolet filters may be selected to give spectral signals with peaks when chemical components of targeted chemical compounds, such as explosives, chemical warfare agents, hazardous chemicals, pollutants, or the like, are present. For another embodiment, array 120 may be cooled, e.g., to reduce noise that may result from infrared heating produced by the infrared radiation passed by the infrared filters.

Figure 2:
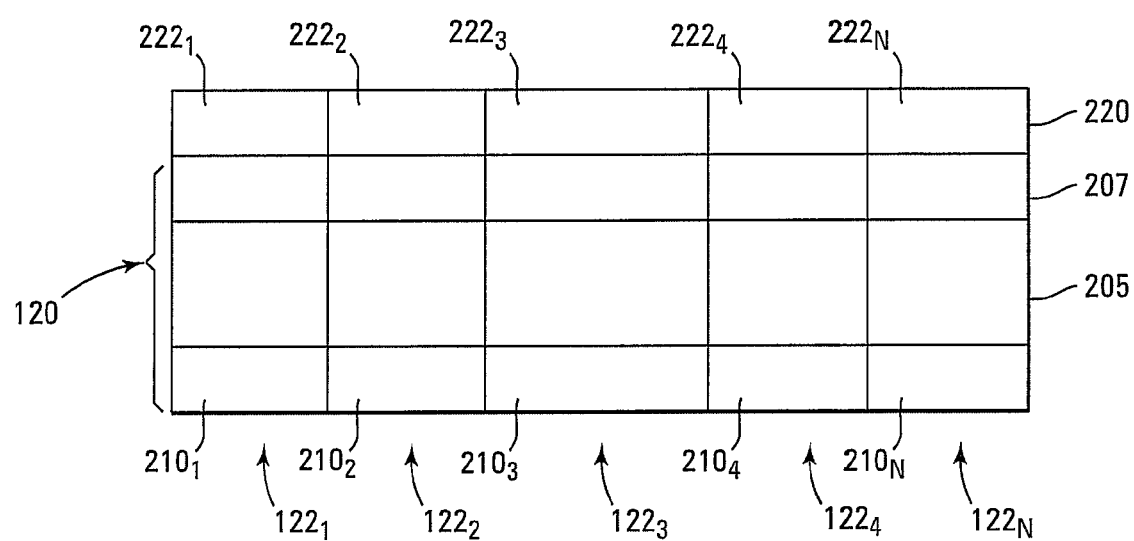
FIG. 2 illustrates a cross-section of a portion of an array of Charged Coupled Device (CCD) radiation sensing elements, according to another embodiment of the disclosure.

FIG. 2 illustrates a cross-section of a portion of array 120 with CCD sensing elements 122, according to another embodiment. For one embodiment, array 120 includes a substrate, e.g., silicon substrate 205. Metal contacts 210 are formed in substrate 205 and respectively form a portion of the CCD sensing elements 122. A portion of substrate 205 may be doped to form a layer 207 of N-type silicon. A filter layer (e.g., or filter mosaic) 220 is formed on a layer 207 overlying metal contacts 210. Filter layer 220 includes filter elements 222 respectively overlying CCD sensing elements 122. For one embodiment, filter elements 222 may be red, blue, and green and near-infrared and mid-infrared filter elements, and/or near ultraviolet filter elements. The silicon of substrate 205 and layer 207 may be doped with arsenic and germanium so that infrared radiation passing through the infrared filter elements can pass through layer 207 and substrate 205 and reach the respective contacts 210. In this way, the CCD array is extended for use in the infrared region. For one embodiment, the CCD array may be extended so that wavelengths of up to about 15 microns can be detected. For another embodiment, filter layer 220 is a Bayer filter (U.S. Pat. No. 3,971,065) modified to include the infrared and/or ultraviolet filter elements.

Each of the radiation sensing elements 122 outputs an analog electrical signal in response to receiving the radiation thereat. Sensor array 120 outputs the analog electrical signals to an analog-to-digital converter 125 (FIG. 1) that digitizes the analog output of each of the CCD radiation sensing elements 122 to obtain a digital output for each of the CCD radiation sensing elements 122 of sensor array 120 of FIG. 1. Analog-to-digital converter 125 outputs the digital signals to a digital signal processor 130 (FIG. 1) for processing.

The digital signals output from analog-to-digital converter 125 contain an image pattern (or mosaic) that may include an image pattern in the visible range similar to an RGBG (red, green, blue, green) Bayer image pattern, where the second green is used for intensity, and a pattern in the infrared range and/or a pattern in the ultraviolet range. For example, digital data for each CCD sensor location, and thus each pixel location, may include a spectral output or signature corresponding to the component of radiation passing through the filter for that CCD sensor location. That is, the data may include spectral signatures with peaks at the red, green, and blue filter locations respectively corresponding to red, green, and blue, radiation components passing through those red, green, and blue filters. In addition, the data may include spectral signatures with peaks at the infrared and/or ultraviolet filter locations respectively corresponding to infrared and/or ultraviolet radiation components passing through those infrared and/or ultraviolet filter locations, where the infrared and/or ultraviolet spectral signatures are respectively produced by chemical components of one or more chemical compounds in the field-of-view of detector 100.

FIG. 3 illustrates an example of an image pattern (or mosaic) 300, according to another embodiment, that may be obtained from the digitized outputs of each of the CCD radiation sensing elements 122. The components $c_1$, $c_2$, and $c_3$ respectively correspond to different filters. For example, for a conventional Bayer image pattern, components $c_1$, $c_2$, and $c_3$ respectively correspond to green, red, and blue filters and thus respectively correspond to spectral signatures with peaks for green, red, and blue radiation. For another embodiment, components $c_1$, $c_2$, and $c_3$ may respectively correspond to different infrared filters, e.g., respectively for passing different wavelengths in the non-visible near- and/or mid-infrared regions, and thus respectively correspond to spectral signatures with peaks in the infrared corresponding to different chemical components of a chemical compound having a spectral signature in the infrared region. Alternatively, components $c_1$, $c_2$, and $c_3$ may respectively correspond to different ultraviolet filters, e.g., respectively for passing different wavelengths in the ultraviolet, and thus respectively correspond to spectral signatures with peaks in the non-visible ultraviolet region corresponding to different chemical components of a chemical compound having a spectral signature in the ultraviolet region.

Although filters corresponding to three different wavelengths in the visible or non-visible regions of the radiation spectrum are exemplified in FIG. 3 and discussed above more than three different visible or non-visible wavelengths may be included. For example, in the infrared region, filters for obtaining spectral signatures with peaks at the wavelengths of about 1.2, 1.9, 2.5, and 3.3 microns may be used. Note that for various embodiments, the image pattern obtained from sensor array 120 may include data corresponding to spectral signatures with peaks for green, red, and blue radiation and data corresponding to spectral signatures with peaks for infrared radiation and/or data corresponding to spectral signatures with peaks for ultraviolet radiation.

Note that since each pixel location corresponding to each CCD sensor location of sensor array 120 is filtered to record only a portion of the total data, each pixel location contains data for only a portion of the total data, and the remaining portion is missing from each pixel. For example, in terms of FIG. 3, where the three radiation components $c_1$, $c_2$, and $c_3$ are considered, each pixel contains ⅓ of the total data, and ⅔ of the total data is missing from each. Where the three radiation components $c_1$, $c_2$, and $c_3$ are respectively green, red, and blue, this means that red and blue are missing from the green, green and red are missing from the blue, etc. Where the three radiation components $c_1$, $c_2$, and $c_3$ respectively correspond to different chemical components of a target chemical compound, $c_2$ and $c_3$ are missing from $c_1$, $c_1$ and $c_2$, are missing from $c_3$, etc.

For conventional CCD cameras configured for detecting color images, demosaicing algorithms are used to interpolate a set of complete red, green, and blue values for each pixel from that pixel and its neighboring pixels, as is known to those of skill in the art. That is, so each pixel contains contributions from the red, green, and blue. In a similar manner, signal processor 130 is configured to use demosaicing algorithms to interpolate a set complete of color and/or spectral chemical signature data at each pixel location from that pixel location and its neighboring pixel locations. In other words, the demosaiced data at each pixel location is representative of the total content of the electromagnetic radiation that is incident on those charge-coupled-device electromagnetic radiation sensing elements. A complete set of spectral chemical signature data at a pixel may contain contributions from each of the different infrared wavelength components that pass through the respective infrared filters or from each of the different ultraviolet wavelength components that pass through the respective ultraviolet filters. For example, in terms of FIG. 3, a complete set of spectral chemical signature data may contain contributions from each of the components $c_1$, $c_2$, and $c_3$.

After determining a set of complete color and/or spectral chemical signature data at each pixel location, this pixel data is transmitted to an image processor 140 (FIG. 1). Image processor 140 converts the complete set of pixel data into an image file, such as a BMP (BitMaP) file, TIFF (Tagged Image File Format) file, JPEG (Joint Photographic Experts Group) file, GIF (Graphics Interchange Format) file, or the like. The image file may then be transferred to a memory 150 of detector 100 for storage, to a display 160, such as a liquid crystal display (LCD), of detector 100, and/or to an input/output interface 170 of detector 100, such as a USB (Universal Serial Bus) interface. For other embodiments, demosaicing may be performed by image processor 140 rather than signal processor 130.

For one embodiment, memory 150 may also contain computer-readable instructions for causing signal processor 130 or image processor 140 to perform the demosaicing of the digital data for each of the CCD sensors 122, for causing image processor 140 to convert the complete set of pixel data into an image file, and for causing signal processor 130 and image processor 140 to perform the various methods described below. For another embodiment, memory 150 may also contain a look-up table of spectral chemical signatures of targeted chemical compounds, such as explosives, chemical warfare agents, hazardous chemicals, pollutants, or the like.

For one embodiment, signal processor 130 may input the spectral chemical signature data at each pixel location into the look-up table stored in memory 150, where the spectral chemical signature data is compared to spectral chemical signatures of targeted chemical compounds. If the spectral chemical signature data matches a spectral chemical signature of a targeted chemical compound in the look-up table, signal processor 130 may cause detector 100 to output an audible and/or visual alarm. For one embodiment, a visual alarm may involve the illumination of a light or the display of a warning message on display 160. For another embodiment, the message may indicate the name of the chemical compound that is detected.

For other embodiments, signal processor 130 may tag the pixels that contain the spectral chemical signatures of the targeted compound so that image processor 140 can assign a certain (e.g., predetermined) color, e.g., that does not typically occur in nature, to the tagged pixels. Therefore, when an image file from 140 is displayed on display 160, display 160 displays the image field captured by the detector with the portions of the captured image field corresponding to the pixels that were tagged colored the certain color assigned to those pixels and the remaining portions of the captured image field displayed in either their normal colors or gray scale, for example. For one embodiment, a different color may be assigned for each different targeted chemical compound to enable the identification of different chemical compounds and their locations within the field of view of detector 100.

For another embodiment, image data files of image processor 140 may be input directly into the look-up table, and image processor 140 may assign certain colors to portions of the image data file that have spectral chemical signatures that match the spectral chemical signatures of the target chemical compounds within the look-up table. For some embodiments, all of the infrared data may be combined to give the temperatures at different locations within the field of view of detector 100.

CONCLUSION

Although specific embodiments have been illustrated and described herein, it will be appreciated by those of ordinary skill in the art that any arrangement that is calculated to achieve the same purpose may be substituted for the specific embodiments shown. Many adaptations of the embodiments will be apparent to those of ordinary skill in the art. Accordingly, this application is intended to cover any adaptations or variations of the embodiments. It is manifestly intended that the embodiments be limited only by the following claims and equivalents thereof.

What is claimed is:

1. A stand-off chemical detector, comprising:
an array of charge-coupled-device electromagnetic radiation sensing elements;
wherein one or more first charge-coupled-device electromagnetic radiation sensing elements of the array are each selectively responsive to a first range of non-visible electromagnetic radiation wavelengths; and
wherein one or more second charge-coupled-device electromagnetic radiation sensing elements of the array are each selectively responsive to a second range of non-visible electromagnetic radiation wavelengths different than the first range of non-visible electromagnetic radiation wavelengths.

2. The stand-off detector of claim 1, wherein a plurality of third charge-coupled-device electromagnetic radiation sensing elements of the array is selectively responsive to a third range of non-visible electromagnetic radiation wavelengths that is different than the first range of non-visible wavelengths and different than the second range of non-visible wavelengths or is selectively responsive to non-visible electromagnetic radiation having the third range of non-visible wavelengths and a fourth range of non-visible wavelengths, the fourth range of non-visible wavelengths being different than the first range of non-visible wavelengths, the second range a non-visible wavelengths, and the third range of non-visible wavelengths.

3. The stand-off detector of claim 1, wherein a silicon substrate on which the charge-coupled-device electromagnetic radiation sensing elements are formed is doped so that the silicon substrate can pass electromagnetic radiation having a wavelength of about 0.35 to about 15 microns.

4. The stand-off detector of claim 3, wherein the silicon substrate is doped so that the silicon substrate can pass electromagnetic radiation having a wavelength of about 0.35 to about 4 microns.

5. The stand-off detector of claim 1, further comprising a processor coupled to the array of charge-coupled-device electromagnetic radiation sensing elements, the processor configured to demosaic outputs of the one or more first charge-coupled-device electromagnetic radiation sensing elements and the one or more second charge-coupled-device electromagnetic radiation sensing elements so that pixel data of pixels of an image field of the detector respectively corresponding to the one or more first charge-coupled-device electromagnetic radiation sensing elements and the one or more second charge-coupled-device electromagnetic radiation sensing elements contains contributions from the first range of non-visible electromagnetic radiation wavelengths and the second range of non-visible electromagnetic radiation wavelengths.

6. The stand-off detector of claim 5, wherein the pixel data of each pixel corresponds to a spectral chemical signature of a chemical present at a location in the image field of the detector that corresponds to the charge-coupled-device electromagnetic radiation sensing element corresponding to that pixel.

7. The stand-off detector of claim 6, wherein the processor is further configured to compare the spectral signature of the chemical compound to spectral signatures of a plurality of target chemical compounds to determine whether the chemical compound is a target chemical compound.

8. The stand-off detector of claim 7, wherein the processor is further configured to assign a certain color to the pixels respectively corresponding to the one or more first charge-coupled-device electromagnetic radiation sensing elements and the one or more second charge-coupled-device electromagnetic radiation sensing elements when the chemical compound is determined to be a target chemical compound.

9. The stand-off detector of claim 8, wherein the stand-off detector is configured to display the certain color on portions of a display of the stand-off detector that correspond to the pixels respectively corresponding to the one or more first charge-coupled-device electromagnetic radiation sensing elements and the one or more second charge-coupled-device electromagnetic radiation sensing elements.

10. The stand-off detector of claim 1, wherein a plurality of third charge-coupled-device electromagnetic radiation sensing elements of the array is selectively responsive to visible electromagnetic radiation.

11. The stand-off detector of claim 10, wherein first, second, and third portions of the plurality of third charge-coupled-device electromagnetic radiation sensing elements are respectively selectively responsive to red; green, and blue visible electromagnetic radiation.

12. The stand-off detector of claim 1, wherein the non-visible electromagnetic radiation having the first range and second range of wavelengths is infrared or ultraviolet electromagnetic radiation.

13. The stand-off detector of claim 1, wherein the one or more first charge-coupled-device electromagnetic radiation sensing elements are coated with first filters that can pass the electromagnetic radiation having the first range of wavelengths and the one or more second charge-coupled-device electromagnetic radiation sensing elements are coated with second filters that can pass the electromagnetic radiation having the second range of wavelengths.

14. The stand-off detector of claim 13, wherein the first and second filters are infrared filters or ultraviolet filters.

15. A chemical detection method, comprising:
  selectively receiving first non-visible radiation having a first range of wavelengths at a plurality of first charge-coupled-device radiation sensing elements of an array of charge-coupled-device radiation sensing elements of a stand-off sensor;
  selectively receiving second non-visible radiation having a second range of wavelengths different than the first range of wavelengths at a plurality of second charge-coupled-device radiation sensing elements of the array of charge-coupled-device radiation sensing elements;
  outputting a first electrical signal from each of the first charge-coupled-device radiation sensing elements in response to receiving the first range of non-visible radiation thereat;
  outputting a second electrical signal from each of the second charge-coupled-device radiation sensing elements in response to receiving the second range of non-visible radiation thereat; and
  demosaicing the first and second electrical signals so that data of first pixels of an image field of the detector respectively corresponding to the first charge-coupled-device electromagnetic radiation sensing elements and data of second pixels of the image field of the detector respectively corresponding to the second charge-coupled-device electromagnetic radiation sensing elements contain contributions from the first and second electrical signals and thus from the first range and second range of non-visible radiation.

16. The method of claim 15, further comprising digitizing the first and second electrical signals before demosaicing the first and second electrical signals.

17. The method of claim 15, further comprising:
  selectively receiving visible radiation at a plurality of third charge-coupled-device radiation sensing elements of the array of charge-coupled-device radiation sensing elements;
  outputting a third electrical signal from each of the third charge-coupled-device radiation sensing elements in response to receiving the visible radiation thereat; and
  demosaicing the third electrical signals along with the first and second electrical signals so that the data of the first and second pixels further contain contributions from the third electrical signals and thus the visible radiation and so that data of third pixels of the image field respectively corresponding to the third charge-coupled-device radiation sensing elements contain contributions from the first, second, and third electrical signals and thus from the first range and second range of non-visible radiation and the visible radiation.

18. The method of claim 17, wherein the visible radiation comprises red, green, and blue radiation.

19. The method of claim 15, wherein the data of each of the first and second pixels corresponds to a spectral signature of a chemical compound that is present in the image field.

20. The method of claim 19, further comprising comparing the spectral signature of the chemical compound to spectral signatures of a plurality of target chemical compounds to determine whether the chemical compound is a target chemical compound.

21. The method of claim 20, wherein comparing the spectral signature of the chemical compound to spectral signatures of the plurality of target chemical compounds comprises inputting the spectral signature of the chemical compound into a look-up table of the stand-off detector that contains the plurality of target chemical compounds.

22. The method of claim 20, further comprising assigning a certain color to the first and second pixels when the chemical compound is determined to be a target chemical compound.

23. The method of claim 22, further comprising displaying the certain color on portions of a display of the stand-off detector that correspond to the first and second pixels.

24. The method of claim 15, further comprising:
  selectively receiving third non-visible radiation having a third range of wavelengths that are different than the first range of wavelengths and the second range of wavelengths at a plurality of third charge-coupled-device radiation sensing elements of the array of charge-coupled-device radiation sensing elements;

outputting a third electrical signal from each of the third charge-coupled-device radiation sensing elements in response to receiving the third range of non-visible radiation thereat; and demosaicing the third electrical signals along with the first and second electrical signals so that the data of the first and second pixels further contain contributions from the third electrical signals and this the third range of non-visible radiation and so that data of third pixels of the image field respectively corresponding to the third charge-coupled-device radiation sensing elements contain contributions from the first, second, and third electrical signals and thus from the first range, second range, and third range of non-visible radiation.

25. A stand-off chemical detector, comprising:

an array comprising at least a plurality of first charge-coupled-device radiation sensing elements and a plurality of second charge-coupled-device radiation sensing elements, wherein the first charge-coupled-device radiation sensing elements respectively correspond to first pixels of an image field of the detector and the second charge-coupled-device radiation sensing elements respectively correspond to second pixels of the image field;

a plurality of first filters, each of the first filters configured to pass first non-visible radiation having a first range of wavelengths to a respective one of the first charge-coupled-device radiation sensing elements;

a plurality of second filters, each of the second filters configured to pass second non-visible radiation having a second range of wavelengths different from the first range of wavelengths to a respective one of the second charge-coupled-device radiation sensing elements;

a processor electrically coupled to the array;

wherein the processor is configured to demosaic outputs of the first charge-coupled-device electromagnetic radiation sensing elements corresponding to the first range of non-visible radiation and the second charge-coupled-device electromagnetic radiation sensing elements corresponding to the second range of non-visible radiation so that first pixel data of the first pixels and second pixel data of the second pixels contain contributions from the first range of non-visible radiation and the second range of non-visible radiation.

* * * * *